(12) United States Patent
Tajima et al.

(10) Patent No.: US 7,045,593 B2
(45) Date of Patent: May 16, 2006

(54) PROCESS FOR SYNTHESIZING PROTEIN USING CELL-FREE PROTEIN SYNTHESIS SYSTEM

(75) Inventors: Kaori Tajima, Kanagawa (JP); Takanori Kigawa, Kanagawa (JP); Mikako Shirouzu, Kanagawa (JP); Takashi Yabuki, Kanagawa (JP); Goushi Ishihara, Kanagawa (JP); Shigeyuki Yokoyama, Kanagawa (JP)

(73) Assignee: Riken, Saitama (JP)

( * ) Notice: Subject to any disclaimer, the term of this patent is extended or adjusted under 35 U.S.C. 154(b) by 0 days.

(21) Appl. No.: 10/476,413

(22) PCT Filed: Apr. 26, 2002

(86) PCT No.: PCT/JP02/04204

§ 371 (c)(1),
(2), (4) Date: Dec. 30, 2003

(87) PCT Pub. No.: WO02/090537

PCT Pub. Date: Nov. 14, 2002

(65) Prior Publication Data

US 2004/0203091 A1    Oct. 14, 2004

(30) Foreign Application Priority Data

May 2, 2001 (JP) ............................. 2001-135111
Sep. 19, 2001 (JP) ............................. 2001-285145

(51) Int. Cl.
*A61K 38/00* (2006.01)
*C12P 21/06* (2006.01)

(52) U.S. Cl. ..................................... 530/333; 435/69.1
(58) Field of Classification Search ............... 435/69.1; 530/333

See application file for complete search history.

(56) References Cited

U.S. PATENT DOCUMENTS 5,270,181 A    12/1993   McCoy et al.
2002/0142387 A1  10/2002   Seki et al.

FOREIGN PATENT DOCUMENTS

EP    1 143 009 A1   10/2001
EP    1 176 210 A1    1/2002
EP    1 354 959 A1   10/2003
JP    09-107954 A     4/1997
WO    WO 99/02671 A1  1/1999

OTHER PUBLICATIONS

Noshimura et al., Enhancement of Protein Synthesis in Continuous-Flow, Cell-Free System by Improvement of Membrane Permeation, 1995, Journal of Fermentation and Bioengineering, 80(4), 403-405.*
Sigma-Aldrich product catalog page for Polyoxyehtylene 23 lauryl ether (Brij 35).*
Bochkareva et al., "Chaperonin-promoted Post-translational membrane insertion of a multispanning membrane protein lactose permease" The Journal of Biological Chemistry, 1996, vol. 271, No. 36, pp. 22256-22261.*
Wheatley et al., "Glycosylation of G-protein-coupled receptors for hormones central to normal reproductive functioning: its occurence and role", Human Reproduction Update, 1999. vol. 5, No. 4, pp. 356-364.*
Norihiro Nishimura et al.: Journal of Fermentation and Bioengineering, (1995), vol. 80, No. 4, pp. 403 to 405.
Takanori Kigawa et al.: FEBS Letters, (1999), vol. 442, pp. 15 to 19.
P.J. Booth et al.: Biochemical Society Transactions, (2000), vol. 2, part 3, p. A50.
E. Bochkareva et al., the Journal of Biological Chemistry, vol. 271, No. 36, Sep. 1996, pp. 22256-22261.

* cited by examiner

*Primary Examiner*—Robert A. Wax
*Assistant Examiner*—Suzanne M. Mayer
(74) *Attorney, Agent, or Firm*—Birch, Stewart, Kolasch & Birch, LLP

(57) ABSTRACT

A method for producing a protein using a cell-free protein synthesis system comprising a detergent so that the protein can be synthesized without aggregation, is provided. The protein is a protein comprising a hydrophobic region in at least a portion thereof, for example, a membrane protein or its fragment (portion). And the detergent is a mild detergent which would not denature the protein, for example, a nonionic or amphoteric ionic detergent.

11 Claims, 8 Drawing Sheets

PROCESS FOR SYNTHESIZING PROTEIN USING CELL-FREE PROTEIN SYNTHESIS SYSTEM

This application is the national phase under 35 U.S.C. § 371 of PCT International Application No. PCT/JP02/04204 which has an International filing date of Apr. 26, 2002, which designated the United States of America.

TECHNICAL FIELD

The present invention relates to a method for producing a protein by using a cell-free protein synthesis system, and, in particular, to a method for producing an insoluble protein that is associated with or implanted in a membrane in vivo, such as a receptor, without aggregation, as well as to a method for reconstituting a protein synthesized thereby.

BACKGROUND ART

A large-scale analysis of genome sequences of various organisms such as human has been studied, and its goal is almost achieved. It is a next task to elucidate functions of proteins, which are encoded in enormous numbers of genes discovered by the sequence analysis. Findings obtained by these protein functions are expected to be greatly useful for the development of new drugs. The analysis of the three dimensional structure of protein provides useful information for elucidating the protein function or drug design. Hereafter, its importance will be increasing and a high throughput analysis in accordance with a large scale analysis will be desirable.

A purified protein in milligram order is necessary for the analysis of the three dimensional structure of protein. Previously, a large-scale preparation of protein was a bottleneck for the three dimensional structural analysis, however, a desired protein can be easily prepared in large-scale, by the advanced gene cloning techniques using an expression system such as that of a microorganism or a cultured cell at the moment. Further, a cell-free protein synthesis system has been improved by various methods such as dialysis and the like, to obtain a protein in milligram order for several hours. Thus, the high throughput analysis of three dimensional structure of protein is coming true.

However, these methods are not always applicable to every kind of proteins, and it is still difficult to prepare a protein that has a hydrophobic region, such as a membrane protein, in large amount. In the expression system of cultured cell, a membrane protein is accumulated in the cell membrane by the localization system of the host cell. Thus, when the expressed protein is purified from the cultured cell, a step to extract the protein from the membrane by using detergents is necessary. This step needs much expense in time and effort, and is not so efficient in the extraction. Some kinds of detergent often impair the intrinsic structure and function of the protein. When a protein that has a hydrophobic region therein, such as a membrane protein is expressed in *E. coli*, the expressed protein often forms insoluble precipitation. Therefore, it is necessary to solubilize the precipitate by using a strong denaturating agent such as guanidine salts or urea, and to renaturate or refold the denatured protein to its intrinsic structure (a folding step) in the purification. These steps are also at much expense in time and effort, and have many problems such as the reprecipitation during the folding step. These proteins also form an insoluble precipitate in a cell-free protein synthesis system, so that the amount of the synthesized protein is not sufficient.

As described above, the problem to solubilize membrane proteins makes it difficult to prepare a large amount of the proteins, and retards the analysis of three dimensional structures of the proteins under the current circumstances. Among membrane proteins, however, there are many important proteins for the target of drug development such as a receptor, channel protein, transporter and the like. The structural analysis of these proteins is urgently necessary for the efficient development of the drug.

DISCLOSURE OF THE INVENTION

It is therefore an object of the present invention to synthesize a hydrophobic protein (a protein comprising a hydrophobic region) such as a membrane protein, in cell-free protein synthesis system without aggregation (insolubilization).

In view of the problems described above, the present inventors have studied, using a cell-free protein synthesis system, the synthesis of an insoluble protein, in particular, a highly hydrophobic protein such as a receptor, which is embedded in the membrane in vivo. The protein has been synthesized without aggregation (insolubilization) by a simple method, that is, an addition of detergents and/or lipids. Thus synthesized protein is found to have biological functions with great probability, even though it is not in the native states in vivo, such as a membrane bound state, and also can be used for the structural and functional analysis of the protein. These findings have led to the completion of the present invention.

According to a first aspect of the present invention, there is provided a method for producing a protein using a cell-free protein synthesis system comprising a detergent to synthesize the protein without aggregation. In a preferred embodiment of the present invention, said protein comprises a hydrophobic region in at least a portion thereof, for example, a whole or portion (a partial structure) of membrane protein and the like.

In a further preferred embodiment of the present invention, said detergent is a mild detergent that does not denature the protein, for example, a nonionic or amphoteric ionic detergent. To be more specific, said detergent is at least one selected from the group consisting of digitonin, polyoxyethylene alkylether (Brij series), polyoxyethylene sorbitan (Tween series), β-dodecylmaltoside, β-octylglucoside, β-nonylglucoside, β-heptylglucoside, β-octylthioglucoside, sucrose mono-decanoate, sucrosemonododecanoate, octyltetraoxyethylene, octylpentaoxyethylene, dodecyloctaoxyethylene, N,N-dimethyldecylamine-N-oxide, N,N-dimethyldodecylamine-N-oxide, N,N-dimethyldodecylammonio propanesulfonate, octyl (hydroxyethyl)sulfoxide, octanoyl-N-methylglucamide, nonanoyl-N-methylglucamide, decanoyl-N-methylglucamide, and (3-[(3-cholamidepropyl)-dimethylammonio]-l-propanesulfonate (CHAPS).

In one embodiment of the present invention, there is provided a method for producing a membrane protein without aggregation by comprising a detergent in a cell-free protein synthesis system using a bacterial cell extract. Said detergent is preferably digitonin in 0.1 to 2.0% by volume and/or Briji35 in 0.01 to 0.5% by volume.

According to a second aspect of the present invention, there is provided a method for reconstituting a protein produced in a cell-free protein synthesis system comprising a nucleic acid template coding for at least a portion of a membrane protein, a detergent, and a lipid, wherein said protein is reconstituted in a lipid bilayer by decreasing the concentration of said detergent in said system simultaneously with the protein synthesis or after a period therefrom.

In a preferred embodiment of the present invention, the step of decreasing the concentration of said detergent is performed by any one or more methods selected from the group consisting of dialysis, dilution, filtration, centrifugation and addition of an adsorbent to said detergent.

Further, in one embodiment of the present invention, there is provided a method for reconstituting a protein comprising the steps of: (a) synthesizing the protein in a cell-free protein synthesis system comprising a cell extract, a nucleic acid template coding for said protein, a detergent and a lipid; and (b) decreasing the concentration of said detergent in the reaction mixture simultaneously with the protein synthesis or after a period therefrom, wherein the synthesized protein has at least a part of its biological activity.

In a preferred embodiment of the present invention, said membrane protein is a protein selected from the group consisting of a receptor, a channel protein, a transporter, and a membrane-bound enzyme, or a portion thereof.

PREFERRED EMBODIMENTS OF THE INVENTION

[Cell-Free Protein Synthesis System]

Figure 1:
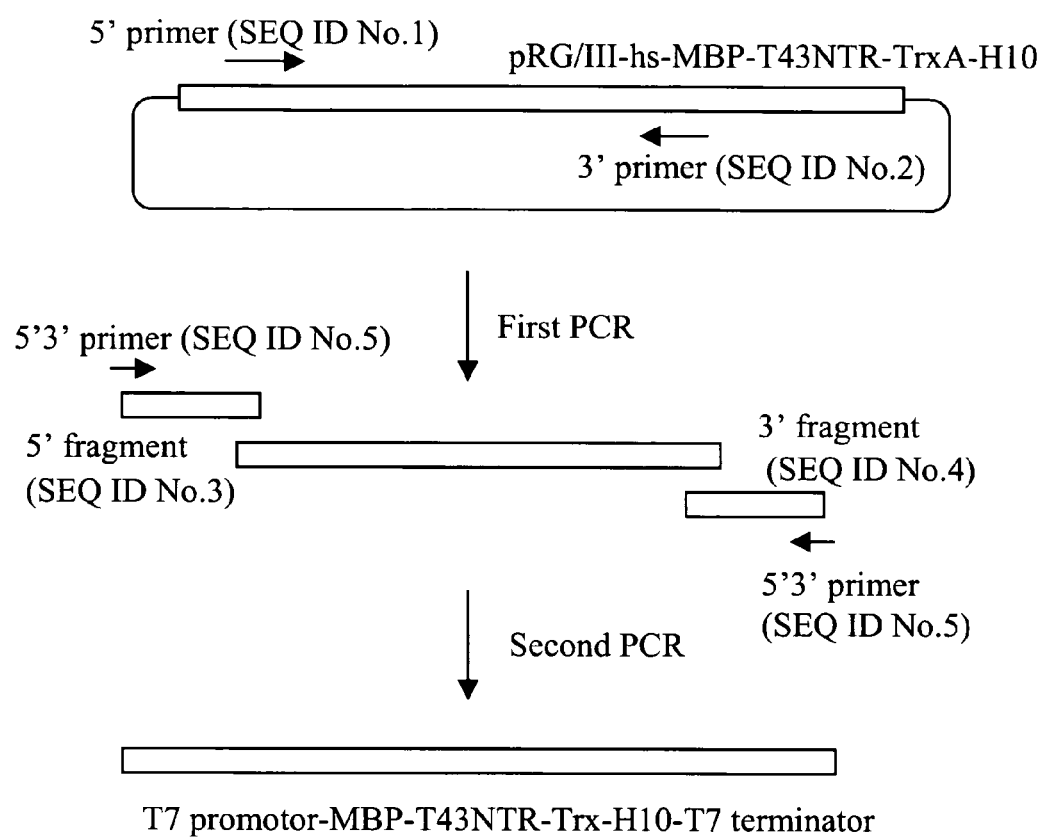
FIG. 1 shows the schematic diagram to prepare the template DNA used for the expression of neurotensin receptor (NTR) in cell-free protein synthesis system, by PCR method.

In the present invention, the cell-free protein synthesis system is an in vitro protein synthesis system using a cell extract. The system may be either a cell-free translation system for producing proteins on ribosome through reading of information of mRNA, or a coupled system comprising a cell-free transcription system that produces mRNA using DNA as a template and a cell-free translation system that translates the mRNA information into proteins. When DNA is used for a template, various kinds of template DNA can be prepared simultaneously and rapidly, by the amplification reaction in vitro such as Polymerase Chain Reaction (PCR), without a complicated procedure of molecular cloning into a living cell, which was previously required.

As the above cell extract, eukaryotic or prokaryotic cell extract containing factors required for protein synthesis such as ribosome, tRNA, and the like can be used. Any eukaryotic or prokaryotic cell which is known in the art can be used. For example, E. coli, thermophilic bacteria, wheat germ, rabbit reticulocyte, murine L-cell, Ehrlich ascitic cancer cell, HeLa cell, CHO cell, and budding yeast can be used. Especially, E. coli cell extract (for example, E. coli S30 cell extract fraction) or Thermus thermophilus cell extract is desirable for the high yield. The E. coli S30 cell extract fraction can be prepared from E. coli A19 strain (rna, met), BL21 strain, BL21 star strain, BL21 codon plus strain, and the like in accordance with generally known methods (refer to Pratt, J. M. et al., Transcription and translation—a practical approach, (1984), pp. 179–209, Henes, B. D. and Higgins, S. J. eds., IRL Press, Oxford), or can be purchased from companies such as Promega or Novagen.

Either a concentrated extract of each of above cell extracts (hereinafter referred to as "concentrated cell extract") or a non-concentrated one (hereinafter referred to as "crude cell extract") can be used as a cell extract, however, a higher yield of synthesized protein can be achieved in the case of concentrated cell extract. To prepare the concentrated cell extract, any method such as ultrafiltration, dialysis, PEG precipitation, and the like can be used.

In addition to the crude cell extracts or concentrated cell extract (10 to 90 weight %) such as E. coli S30 fraction, the cell-free protein synthesis system of the present invention may contain DNA or RNA (mRNA and the like) coding for target proteins, ATP (0.5 to 5 mM), GTP (0.05 to 1.0 mM), CTP (0.05 to 1.0 mM), UTP (0.05 to 1.0 mM), buffer solutions, salts, amino acids, RNase inhibitors, antibacterial agents, RNA polymerase if necessary (in case where DNA is used as a template), and tRNA and the like. In addition, it can contain ATP regenerating systems, polyethyleneglycol (for example, PEG#8000), 3', 5'-cAMP, folic acids (0.1 to 5 mM), reducing agents (for example, 1 to 10 mM dithiothreitol) and the like.

For the buffer solution, for example, buffer agent such as Hepes-KOH or Tris-OAc can be used. For salts, acetate (for example, ammonium salts, magnesium salts and the like) or glutamate salts can be used. For antibacterial agents, sodium azide or ampicillin can be used. In case where DNA is used for the template, RNA polymerase is added to the reaction system, and enzymes on the market such as T7 RNA polymerase can be used.

In the present invention, a combination of 0.02 to 5 μg/μL of creatine kinase (CK) and 10 to 100 mM of creatine phosphate (CP) is preferably used as the ATP regenerating system, but is not limited only to this system. Any material which is known on the prior art can be used. In addition to the combination described above, for example, a combination of 1 to 20 mM of phosphoenolpyruvate (PEP) and 0.01 to 1 μg/μL of pyruvate kinase (PK) also can be used. PK and CK are enzymes which regenerate ADP to ATP, and require PEP and CP as the substrate respectively.

The cell-free protein synthesis system of the present invention can be carried out by a batch method, flow method, and any other techniques previously known, for example, those methods are ultrafiltration method, dialysis method, column chromatography method using a resin on which templates for translation are immobilized (refer to Spirin, AS. et al., Meth. In Enzymol. volume 217, pp. 123–142, 1993), and the like.

[Insoluble Proteins]

A protein to be synthesized in the present invention is a protein that comprises a highly hydrophobic region locally in the molecule (insoluble protein), or a portion thereof. Examples of the protein are, in particular, membrane proteins such as a receptor, a channel protein, a transporter, and a membrane-bound enzyme. To be more specifically, the membrane receptors are exemplified by ion channel-contained receptors such as glutamate receptors in brain, seven membrane-spanning type receptors (aminergic receptors such as adrenergic and dopaminergic, and receptors for bioactive peptides such as angiotensin and neuropeptides), adipose receptors such as prostaglandin receptors, peptide hormone receptors such as ACTH and TSH receptor, and chemokine receptors. The transporters are exemplified by those transporting relatively small molecules such as glucose and amino acid, furthermore relatively large molecules such as proteins and DNAs. As the membrane-bound enzyme, a number of proteins such as G protein that participate in the signal transduction into cells exist, and play important rolls concerning cell proliferation and malignant transformation. In addition to these previously known membrane proteins, the protein include novel membrane proteins that have unknown functions.

In some cases, these insoluble proteins may be used to analyze the biological functions and three dimensional structures surprisingly by complexing with detergents. For example, soluble fractions of mouse brain extracted with detergents were reported to be detected the binding activity with neurotensin (refer to Mazella, J. et al., J. Biol. Chem. 263, p. 144–149, 1988). In addition, a photosynthetic reaction center complex of rhodobacter (Rhodopseudomonas viridis) has been crystallized as a complex with detergents, and a crystal structure of the complex was solved in a high resolution more than 3 Å (refer to Michel, H. et al., J. Mol. Biol., 158, p. 567-, 1982; and Deisenhofer, J. et al., Nature 916, p. 618- (1985)). Thus, membrane proteins are likely to be reconstructed to their original states in lipid bilayer, even though they are crystallized under conditions of covering with substantial amount of detergents.

Therefore, the protein synthesized according to the method of the present invention without aggregation, and recovered from supernatant of the reaction mixture has a high possibility to exert biological function such as ligand binding activities or signal transducing activities.

[Detergents]

The detergent to be used in the present invention is preferably selected and used appropriately in connection with distinct kinds of proteins to be synthesized. Any detergent known in the art, which does not denature the proteins can be used. Such detergents which are usually used, are roughly classified into a nonionic, anionic, and amphoteric ionic detergent in connection with its electronic property. The nonionic detergents are exemplified by digitonin, polyoxyethylene alkylether (Brij series), polyoxyethylene sorbitan (Tween series), β-dodecylmaltoside, β-octylglucoside, β-nonylglucoside, β-heptylglucoside, β-octylthioglucoside, sucrose mono-decanoate, sucrose mono-dodecanoate, octyltetraoxyethylene, octylpentaoxyethylene, and dodecyloctaoxyethylene. The anionic detergents are, for example, taurodeoxycholic acid and the like. The amphoteric ionic detergents are exemplified by N,N-dimethyldecylamine-N-oxide, N,N-dimethyldodecylamine-N-oxide, N,N-dimethyldodecylammonio propanesulfonate, octyl (hydroxyethyl)sulfoxide, octanoyl-N-methylglucamide, nonanoyl-N-methylglucamide, decanoyl-N-methylglucamide, and (3-[(3-cholamidepropyl) dimethylammonio]-1-propanesulfonate (CHAPS).

These detergents can be used as single species, or combine more than two species. The working concentration of these detergents is preferably adjusted depending on the kinds of target proteins, however, the concentration of usually used is preferably 1 to 50 times of critical micelle concentration (CMC) of the detergent, more preferably 3 to 10 times thereof. For example, in case where the nonionic detergents such as digitonin and Briji35 are used as a detergent, the concentration of digitonin is preferably 0.1 to 2.0% by volume, more preferably 0.4 to 1.5% by volume. The concentration of Brij35 is preferably 0.01 to 0.5% by volume, more preferably 0.02 to 0.2% by volume.

The above detergent is preferably a mild detergent that does not denature the protein. Detergents that have a strong potency of protein denaturation such as sodium dodecyl sulfate (SDS) is likely to denature the synthesized protein. In addition, these detergents are not appropriate for the method of the present invention due to the possibility to denature the enzyme protein consisting of the cell-free system and inhibit the protein synthetic activity thereof.

Further, in case where the detergent by itself is not sufficient to sustain the protein structure in aqueous solution and to prevent the aggregation, it is capable of preventing the aggregation for the protein to be coexisted with amphiphilic substances such as heptane-1,2,3-triol and octane-1,2,3-triol, which are smaller than the above detergent or lipid, and with polar substances such as triethylamine ammonium and phenylalanine.

[Detection of Synthesized Proteins and Reconstitution Thereof]

The protein synthesized in the cell-free protein synthesis system according to the method of the present invention is detected in the supernatant after normal centrifugation of the reaction mixture, without aggregation (precipitation) in the reaction mixture by complexing with the detergent, as concretely shown in the following examples. Thus, the protein in the solution can be used to analyze the function and the structure by NMR, further to crystallize the protein from the solution to analyze the X-ray crystal structure.

It is further preferable to reconstitute the protein synthesized in the cell-free protein synthesis system with artificial membranes, liposomes or the like, in order to analyze the structure and function of the membrane protein or the like in vivo more precisely. The synthesized protein is reconstituted in a lipid membrane by decreasing the concentration of detergent simultaneously with the protein synthesis or after a certain period from the protein synthesis, in a cell-free protein synthesis system supplemented with the detergent and lipid. As used herein, the term "reconstitution" refers to the construction of the system that is homologous to the state in vivo by embedding at least a portion of the synthesized membrane protein in artificial membranes or liposomes which are constituted of lipid bilayer or multi-layer. The lipids which can be used for this method comprises simple lipid such as acylglycerol (neutral lipid), cholesterol ester and the like, and complex lipid such as phospholipid and glycolipid. Phospholipds include phosphatidylcholine (PC), phosphatidylethanolamine (PE), phosphatidylserine (PS), phosphatidylinositol (PI), phosphatidylglycerol (PG), plasmalogen, sphingomyelin, ceramide ciliatin, and derivatives thereof, while glycolipids are exemplified by cerebroside, globoside, ganglioside and the like, which are generically called sphingoglycolipid. One or more of these lipids may be used in combination, in an amount of usually 0.1 to 10 mM, which should be properly adjusted depending on the used lipid.

The membrane protein synthesized in the presence of these lipids is reconstituted by incorporating therein, when the lipid bilayer or multi-layer is formed by decreasing the concentration of detergent. Methods for decreasing the concentration of detergent are exemplified by dialysis, dilution, and addition of an adsorbent to the detergent.

When the membrane protein that has been reconstituted in the lipid membrane is purified, it is possible to recover these complex by filtration, centrifugal separation or the like, and further to solubilize the protein once more by adding the detergent to purify the target protein. Example 3 as described below, shows that the membrane protein thus purified and reconstituted in the lipid membrane has a ligand binding activity as human β2-adrenergic receptor (ADRB2). The ligand binding activity is assayed by measuring a specific binding (incorporation) of radioisotope of an antagonist, which binds or inhibits competitively with the protein in the various molar ratio of the radio-labeled or non-labeled antagonist of β-adrenergic receptor such as Alprenolol. According to the results of FIG. 11, the reconstituted β-adrenergic receptor is recognized to have a biological function to bind specifically with its ligand, because the radio-labeled amount that binds to β-adrenergic receptor is decreasing when the concentration of non-labeled antagonist is increased.

Further, in case where the cell-free system is constituted of dialysis method, it is possible to reconstitute the synthesized protein in the lipid layer by adding the detergent and lipid into the internal dialysate of the synthetic reaction, and removing the detergent from the external dialysate simultaneously with the protein synthesis or after a period from the protein synthesis, to optimize the concentration of detergent in accordance with the rate of protein synthesis.

EXAMPLES

The present invention is explained in more detail by reference to the following examples using cDNA fragments coding for a rat neurotensin receptor (NTR) and a human β2-adrenergic receptor (ADRB2). These examples, however, do not restrict the scope of the present invention. Incidentally, "%" means "volume %" unless otherwise specified in the specification.

Example 1

Synthesis of a Rat Neurotensin Receptor (NTR)

NTR is a member of G protein coupled receptors, a seven-spanning membrane protein. By binding with neurotensin as a ligand, the receptor exhibits a function to activate phospholipase C through G protein, and to produce inositol-1,4,5-trisphosphate/diacylglycerol.

Preparation of Template DNA Fragments Encoding MBP-T43NTR-TrxA-H10

In this example, a fusion gene that is prepared by ligating a maltose binding protein (MBP) gene at the 5' region of NTR cDNA, and ligating a thioredoxin (TrxA) gene and 10 histidine tag sequences at the 3' region of NTR cDNA was used. The expression vector comprising this fusion gene (pRG/III-hs-MBP-T43NTR-TrxA-H10) was reported to express and produce the fusion protein in E. coli (refer to Grisshammer, R. et al., Biochemical Society Transactions, vol. 27, pp. 899–903, 1999), and kindly provided by Dr. Watts (Oxford University). The plasmid vector pRG/III-hs-MBP-T43NTR-TrxA-H10 comprising NTR cDNA was used as a template, and the 5' primer: 5'-GTTTAACTTTAA-GAAGGAGATATACATATGAAAATAAAAA-CAGGTGCACG CA-3' (SEQ ID NO:1) and 3' primer: 5'-GCGGATAACAATTTCACACAGGAAACA GTC-GACGCCAGGGTTTTCCCAGT-3' (SEQ ID NO:2) were used for preparing the reaction mixture (25 μL) of the composition shown in Table1. The first PCR was carried out according to the program shown in Table 2 and NTR cDNA fragment was amplified.

TABLE 1

Composition of the first PCR mixture

| Composition | Concentration | Amount |
| --- | --- | --- |
| Template plasmid | 2 ng/μL | 5 μL |
| 5' primer | 2.5 μM | 5 μL |
| 3' primer | 2.5 μM | 5 μL |
| dNTPs (Toyobo) | 2 mM | 2.5 μL |
| 10 × Expand HF buffer (Boehringer Mannheim) containing 15 mM MgCl$_2$ | | 2.5 μL |
| Sterilized Distilled water | | 4.8 μL |
| DNA polymerase (Boehringer Mannheim) | 3500 units/mL | 0.2 μL |

TABLE 2

Program for the PCR

| STEP 1 | 94° C. | 2 min |
| --- | --- | --- |
| STEP 2 | 94° C. | 30 sec |
| STEP 3 | 60° C. | 30 sec |
| STEP 4 | 72° C. | 2 min |
| STEP 5 | GOTO 2 for 9 times | |
| STEP 6 | 94° C. | 30 sec |
| STEP 7 | 60° C. | 30 sec |
| STEP 8 | 72° C. | 2 min + 5 sec/cycle |
| STEP 9 | GOTO 6 for 19 times | |
| STEP 10 | 72° C. | 7 min |
| STEP 11 | 4° C. | forever |

Next, 25 μL of the reaction mixture whose composition was shown in Table 3 were prepared using the first PCR product as a template, two chemically synthesized double stranded DNA fragments, which are partially overlapping with the template at its both terminals (5' fragment encoding T7 promoter sequence (SEQ ID No. 3) and 3' fragment encoding T7 terminator sequence (SEQ ID No. 4)), and 5', 3' primer: 5'-GCCGCTGTCCTCGTTCCCAGCC-3' (SEQ ID No. 5). The reaction mixture was used for the second PCR according to the program shown in Table 2. As a result, the template cDNA fragment of NTR fusion protein (MBP-T43NTR-TrxA-H10) inserted between the 5' upstream T7 promoter sequence and 3' downstream T7 terminator sequence was obtained as shown in FIG. 1. The fusion protein comprises a maltose binding protein (MBP), a partially deleted NTR (T43NTR) at its N-terminal region, a thioredoxin (TrxA) and ten histidine tag sequences.

TABLE 3

Composition of the second PCR mixture

| Composition | Concentration | Amount |
| --- | --- | --- |
| First PCR product (template) | | 10 μL |
| 5', 3' primer | 100 μM | 0.25 μL |
| 5' fragment | 2 nM | 0.625 μL |
| 3' fragment | 2 nM | 0.625 μL |
| dNTPs (Toyobo) | 2 mM | 2.5 μL |
| 10 × Expand HF buffer (Boehringer Mannheim) containing 15 mM MgCl$_2$ | | 2.5 μL |
| Sterilized Distilled water | | 8.3 μL |
| DNA polymerase (Boehringer Mannheim) | 3500 units/mL | 0.2 μL |

Synthesis of MBP-T43NTR-TrxA-H10 Protein by Cell-free Protein Synthesis System

E. coli S30 extract was prepared from E. coli BL21 strain in accordance with the method of Zubay et al., (Ann. Rev. Geneti., 7, 267–287, (1973)). The reaction mixture for protein synthesis was constituted of the composition shown in the following Table 4 supplemented with 1 μL of the above PCR product of MBP-T43NTR-TrxA-H10 cDNA fragment and 7.2 μL of the above E. coli S30 extract in 30 μL of total volume. The reaction mixtures of the same composition except for addition of 0.04%, 0.4%, or 1% digitonin (Wako pure chemical industries, Ltd.) in final concentration, or 0.01%, 0.02% or 0.2% Brij35 (SIGMA) in final concentration were prepared respectively. The protein synthesis reaction was performed at 30° C. for two hours.

TABLE 4

Composition of protein synthesis reaction mixture

| Composition | Concentration |
| --- | --- |
| Hepes-KOH (pH7.5) | 58.0 mM |
| Dithiothreitol | 2.3 mM |
| ATP | 1.2 mM |
| CTP, GTP, UTP | Each 0.9 mM |
| Creatine phosphate | 81.0 mM |
| Creatine kinase | 250.0 μg/mL |
| Polyethylene glycol 8000(PEG8000) | 4.00% (w/v) |
| 3', 5' cyclic AMP(cAMP) | 0.64 mM |
| L-(−)-5,6,7,8-tetrahydrofolate | 35.0 μg/mL |
| E. coli total t-RNA | 170.0 μg/mL |
| Potassium glutamate | 200.0 mM |
| Ammonium acetate | 27.7 mM |
| Magnesium acetate | 10.7 mM |
| 20 kinds of amino acid | Each 1.0 mM |
| T7 RNA polymerase (Toyobo) | 16.0 units/μL |

Detection of MBP-T43NTR-TrxA-H10 Protein by Western Blotting Using Anti-histidine Tag Antibody After the synthesis reaction, the reaction mixture was centrifuged at 12,000×g, for 20 minutes, and separated into a supernatant and a precipitate. The precipitate was dissolved in one and a-half volume of SDS-sample buffer. The supernatant was treated with acetone and the obtained precipitate was dissolved in one and a-half volume of SDS-sample buffer. These samples were loaded on SDS-Polyacrylamide gel electrophoresis using MULTIGEL 15/25 (Daiichi Pure Chemicals) as a gel matrix. After the electrophoresis, using Semidry transfer apparatus BE-330

(BIOCRAFT Co., Ltd,) the protein samples in the gel were blotted to nitrocellulose membranes (PROTORAN BA85, pore size of 0.45 µm, Schleicher & Schuell). The nitrocellulose membranes were blocked with 10-fold diluted Western Blocking Reagent (Roche) at room temperature for overnight. As a first antibody, 1000-fold diluted anti-histidine tag antibody (6×His Monoclonal Antibody, CLONTECH) was added to the membrane and incubated with the membranes at room temperature for one hour. The nitrocellulose membranes were washed four times with TBST solution, and then, as a second antibody, 5000-fold diluted anti-mouse IgG antibody (conjugated with horseradish peroxidase, Amersham Pharmacia Biotech) was added to the membranes and further incubated at room temperature for one hour. After washing the nitrocellulose membrane with TBST solution for four times, the membranes were reacted with ECL Western Blotting Detection Reagent (Amersham Pharmacia Biotech) and examined (detected) by a lumino-image analyzer LAS-1000 plus (Fuji Photo Film Co. Ltd. Japan).

Synthesis of MBP-T43NTR-TrxA-H10 Protein by Addition of Digitonin

Figure 2:
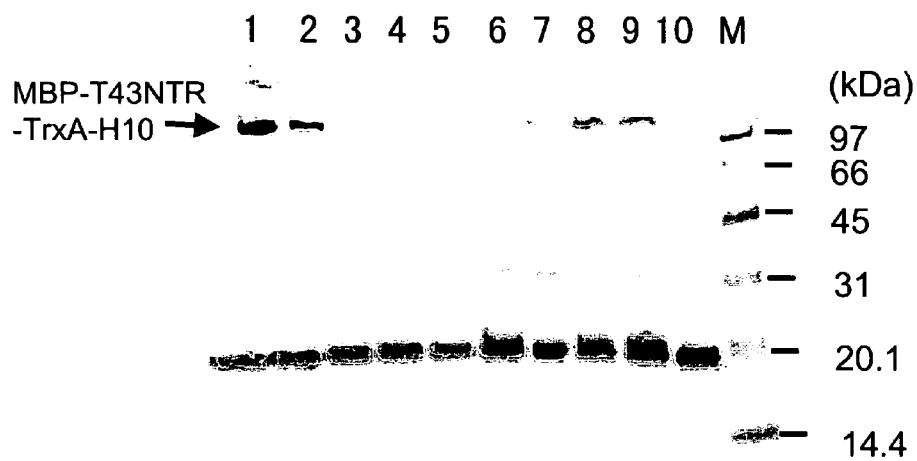
FIG. 2 shows the results of SDS-Polyacrylamide Gel Electrophoresis of neurotensin receptors (NTR), which were synthesized in cell-free protein synthesis system added with digitonin, by western blotting analysis. Insoluble fractions precipitated by centrifugation after synthesis reactions were applied in lanes 1 to 5, and the supernatant fractions of the centrifugation were applied in lanes 6 to 10. The amounts of digitonin added to the reaction mixture were 0% (lanes 1 and 6), 0.04% (lanes 2 and 7), 0.4% (lanes 3 and 8), 1% (lanes 4 and 9) and 0% without template DNAs (lanes 5 and 10), respectively. Lane M was the molecular weight marker (ECL protein molecular weight markers by Amersham Pharmacia Biotech).

The result of Western blotting analysis of proteins synthesized in the presence or absence of digitonin was shown in FIG. 2. The detected bands correspond to the protein that is recognized by anti-histidine tag antibody, that is, MBP-T43NTR-TrxA-H10. Incidentally, about 20 kDa bands were detected in all samples including control samples (lanes 5 and 10) without template DNA, thus, they are considered to be proteins derived from *E. coli*, to which the antibody binds nonspecifically. In the absence of digitonin, the synthesized MBP-T43NTR-TrxA-H10 was insoluble (lane 1), and was not detected in the supernatant (lane 6). In the presence of 0.04% digitonin, although most of the proteins were insoluble (lane 2), a small amount of the protein was detected in the supernatant fraction (lane 7). In the presence of 0.4% or more of digitonin, it was found that most of MBP-T43NTR-TrxA-H10 were detected in the supernatant (lanes 8 and 9), and little remained in the insoluble fraction (lanes 3 and 4). These results indicated that a membrane protein MBP-T43NTR-TrxA-H10 could be recovered from the supernatant by the method of the present invention.

Synthesis of MBP-T43NTR-TrxA-H10 Protein by Addition of Brij 35

Figure 3:
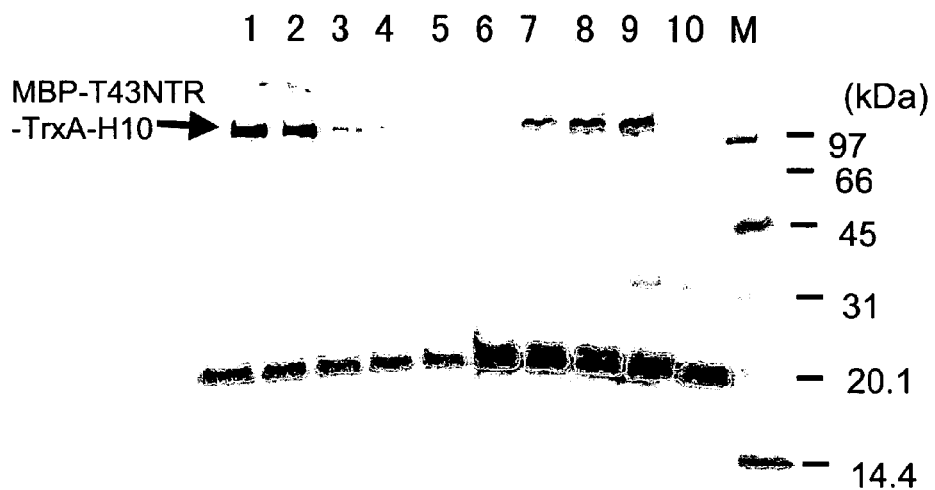
FIG. 3 shows the results of SDS-Polyacrylamide Gel Electrophoresis of neurotensin receptors (NTR), which were synthesized in cell-free protein synthesis system added with Brij35, by the western blotting analysis. Insoluble fractions precipitated by centrifugation after synthesis reactions were applied on lanes 1 to 5, and the supernatant fractions of the centrifugation were applied on lanes 6 to 10. The amounts of Brij35 added to the reaction mixture were 0% (lanes 1 and 6), 0.01% (lanes 2 and 7), 0.02% (lanes 3 and 8), 0.2% (lanes 4 and 9) and 0% without template DNAs (lanes 5 and 10), respectively. Lane M was the molecular weight marker (ECL protein molecular weight markers by Amersham Pharmacia Biotech).

The result of Western blotting analysis of proteins synthesized in the presence or absence of Brij35 was shown in FIG. 3. The detected bands correspond to the protein that is recognized by anti-histidine tag antibody, that is, MBP-T43NTR-TrxA-H10. Incidentally, about 20 kDa bands were detected in all samples including control samples (lanes 5 and 10) without template DNA, thus, they are considered to be proteins derived from *E. coli*, to which the antibody binds nonspecifically. In the absence of Brij35 and in the presence of 0.01% Brij35, the synthesized MBP-T43NTR-TrxA-H10 was insoluble (lanes 1 and 2), and was not detected in the supernatant (lanes 6 and 7). In the presence of 0.02% Brij35, although a portion of the synthesized MBP-T43NTR-TrxA-H10 was detected in the insoluble fraction (lane 3), most of the proteins were detected in the supernatant fraction (lane 8). In the presence of 0.2% Brij35, only a small amount of MBP-T43NTR-TrxA-H10 was insoluble (lane 4), and almost all amount of the protein were detected in the supernatant (lane 9). These results indicated that a membrane protein MBP-T43NTR-TrxA-H10 can be recovered from the supernatant in the system using Brij35 as well as that of digitonin.

Example 2

Synthesis of a Human β2-Adrenergic Receptor (ADRB2)

ADRB2 is a member of G protein coupled receptors, a seven-spanning membrane protein. By binding with adrenaline as a ligand, the receptor exhibits a function to activate adenylyl cyclase through acceleratory G protein, and to increase the concentration of intracellular cyclic AMP. The protein has already known, and the nucleotide sequence of the cDNA was registered in GenBank (Accession No. AF022956).

Preparation of Template DNA Fragments Encoding His6-$\beta_2$

In this example, plasmid vector pFASTBacβ2-Gs comprising human β2-adrenergic receptor and bovine Gs fusion cDNA (obtained from Dr. Robert J. Lefkowitz (Duke University medical center) was used as a template, and the 5' primer: 5'-GGTGCCACGCGGATCCATGGGGCAAC-CCGGGAAC-3' (SEQ ID NO:6) and 3' primer: 5'-GCG-GATAACAATTTCACACAGGAAACAGTC-GACTTACAGCAGTG AGTCATTTGTACTACAA-3' (SEQ ID NO:7) were used for preparing the reaction mixture (25 µL) of the composition shown in Table 1 by the similar manner as the method in Example 1. The first PCR was carried out according to the program shown in Table 2 and ADRB2 cDNA fragment was amplified.

Figure 4:
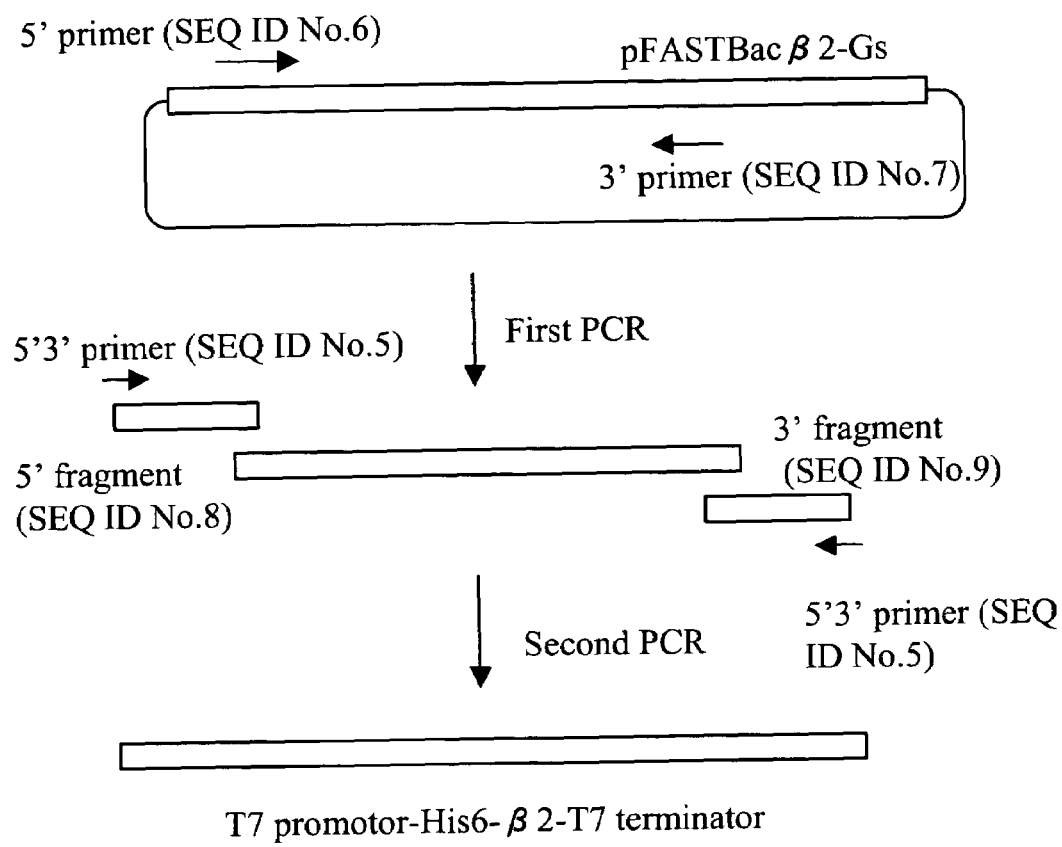
FIG. 4 shows the schematic diagram to prepare the template DNA used for the expression of human β2-adrenergic receptor (ADRB2) in cell-free protein synthesis system, by PCR method.

Next, 25 µL of the reaction mixture whose composition was shown in Table 3 were prepared using the first PCR product as a template, two chemically synthesized double stranded DNA fragments, which are partially overlapping with the template at its both terminals (5' fragment encoding T7 promoter sequence, six histidine tag sequences and thrombin cleavage site (SEQ ID No. 8) and 3' fragment encoding T7 terminator sequence (SEQ ID No. 9)), and 5', 3' primer: 5'-GCCGCTGTCC TCGTTCCCAGCC-3' (SEQ ID No. 5) by the similar manner as the method in Example 1. The reaction mixture was used for the second PCR according to the program shown in table 2. As a result, the template cDNA fragment of ADRB2 (His6-$\beta_2$) was obtained as shown in FIG. 4. The template cDNA fragment thus obtained has T7 promoter sequence, histidine tag sequence and thrombin cleavage site at the 5' region thereof, and T7 terminator sequence at the 3' region thereof.

Synthesis of His6-$\beta_2$ Protein by Cell Free System

*E. coli* S30 extract was used for synthesizing His6-$\beta_2$ protein by cell free system according to the similar manner as the method in Example 1. The reaction mixture for protein synthesis was constituted of the composition shown in the table 4 supplemented with 1 µL of the above His6-$\beta_2$ template cDNA fragment and 7.2 µL of the above *E. coli* S30 extract in 30 µL of total volume. The reaction mixtures of the same composition except for addition of 0.04%, 0.4%, or 1% digitonin (Wako pure chemical industries, Ltd.) in final concentration, 0.01%, 0.02% or 0.2% Brij35 (SIGMA) in final concentration, or 0.5% β-dodecylmaltoside, NP-40, Tween20 or Triton X-100 in final concentration were prepared respectively. In case of detecting the protein by autoradiography, 3.7 kBq L-[$^{14}$C]Leucine (Moravek Biochemicals) was added thereto. The protein synthesis reaction was performed at 30° C. for 120 minutes.

Detection of His6-$\beta_2$ Protein by Autoradiography

After the synthesis reaction, the reaction mixture was centrifuged at 12,000×g, for 20 minutes, and separated into a supernatant and a precipitate. The precipitate thus obtained was dissolved in one and a-half volume of SDS-sample buffer. The supernatant was treated with acetone and the obtained precipitate was dissolved in one and a-half volume of SDS-sample buffer. These samples were loaded on SDS-Polyacrylamide gel electrophoresis using MULTIGEL 15/25 (Daiichi Pure Chemicals) as a gel matrix. After the electrophoresis, the gel was dried, and the dried gel was allowed to stand with Imaging Plate (BAS-SR2040, Fuji Photo Film Co. Ltd. Japan) for 24 hours in a dark place. Subsequently, the detection of the labeled protein was performed by using a bio-imaging analyzer BAS2500 (Fuji Photo Film Co. Ltd. Japan).

Detection of His6-$\beta_2$ Protein by Western Blotting Using Anti-histidine Tag Antibody The reaction mixture after the synthesis reaction was separated into a supernatant and a precipitate, and subjected to SDS-PAGE by the similar manner as the method in Example 1. Subsequently, the protein samples in the gel were blotted to nitrocellulose membranes, reacted with anti-histidine tag antibody and examined by a lumino-image analyzer LAS-1000 plus (Fuji Photo Film Co. Ltd. Japan) according to the similar manner as the method in Example 1.

Synthesis of His6-$\beta_2$ Protein by Addition of Digitonin

Figure 5:
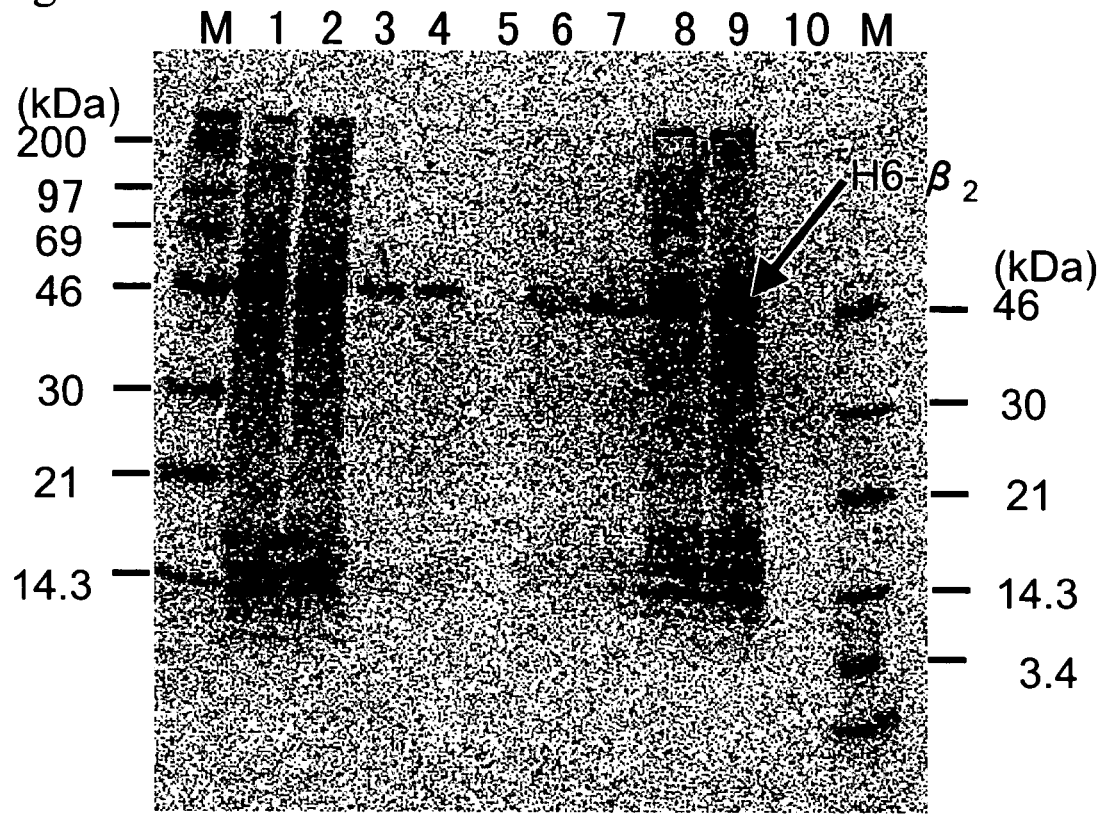
FIG. 5 shows the result of SDS-Polyacrylamide Gel Electrophoresis of human β2-adrenergic receptor (ADRB2) synthesized in cell-free protein system comprising digitonin, and analyzed by autoradiography. Insoluble fractions precipitated by centrifugation after synthesis reactions were applied on lanes 1 to 5, and the supernatant fractions after the centrifugation were applied on lanes 6 to 10. The amount of digitonin added to the reaction mixture were 0% (lanes 1 and 6), 0.04% (lanes 2 and 7), 0.4% (lanes 3 and 8), 1% (lanes 4 and 9) and 0% without template DNAs (lanes 5 and 10), respectively. Lane M was the molecular weight marker (ECL protein molecular weight markers by Amersham Pharmacia Biotech).
Figure 6:
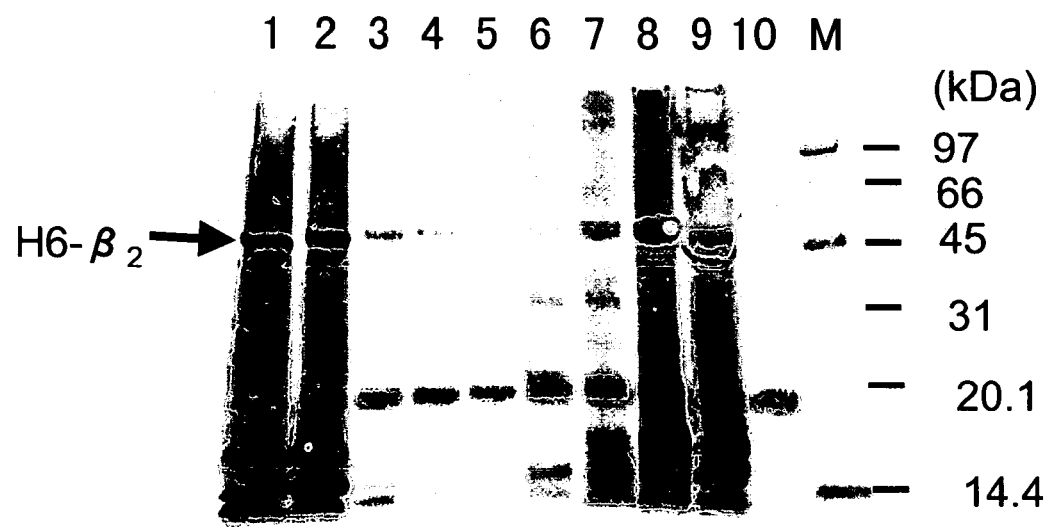
FIG. 6 shows the results of SDS-Polyacrylamide Gel Electrophoresis of human β2-adrenergic receptor (ADRB2) synthesized in cell-free protein synthesis system comprising digitonin, by the western blotting analysis. Insoluble fractions precipitated by centrifugation after synthesis reactions were applied on lanes 1 to 5, and the supernatant fractions of the centrifugation were applied on lanes 6 to 10. The amounts of digitonin added to the reaction mixture were 0% (lanes 1 and 6), 0.04% (lanes 2 and 7), 0.4% (lanes 3 and 8), 1% (lanes 4 and 9) and 0% without template DNAs (lanes 5 and 10), respectively. Lane M was the molecular weight marker (ECL protein molecular weight markers by Amersham Pharmacia Biotech).

The result of autoradiography of proteins synthesized in the presence or absence of digitonin was shown in FIG. 5, and also the result of Western blotting analysis of that was shown in FIG. 6. In FIG. 5 the labeled protein bands synthesized in the absence of digitonin and presence of 0.04% digitonin, were mainly detected in the precipitate fraction (lanes 1 and 2) and little was detected in the supernatant (lane 6 and 7), and it was indicated that, in these condition, most of the proteins in the sample was insoluble. On the other hand, in case that the concentration of digitonin was 0.4% and 1%, the labeled protein bands were mainly detected in the supernatant (lanes 8 and 9). These results indicated that the synthesized proteins were prevented from being insoluble and these proteins could be recovered from the supernatant by adding a certain concentration or more of digitonin to the cell free protein synthesis system.

On the other hand, in the result of Western blotting analysis by anti-histidine tag antibody (FIG. 6), about 20 kDa bands were detected in all samples including control samples (lanes 5 and 10) without template DNA, thus, they are considered to be proteins derived from E. coli, to which the antibody binds nonspecifically. In the absence of digitonin, the synthesized His6-$\beta_2$ was insoluble (lane 1), and was not detected in the supernatant (lane 6) as the result of FIG. 5. In the presence of 0.04% digitonin, although most of the proteins were insoluble (lane 2), a small amount of the protein was detected in the supernatant fraction (lane 7). In the presence of 0.4% or more of digitonin, most of His6-$\beta_2$ were detected in the supernatant fraction (lanes 3, 4, 8 and 9). These results indicated that a membrane protein His6-$\beta_2$ could be recovered from the supernatant by the method of the present invention.

Synthesis of His6-$\beta_2$ Protein by Addition of Brij 35

Figure 7:
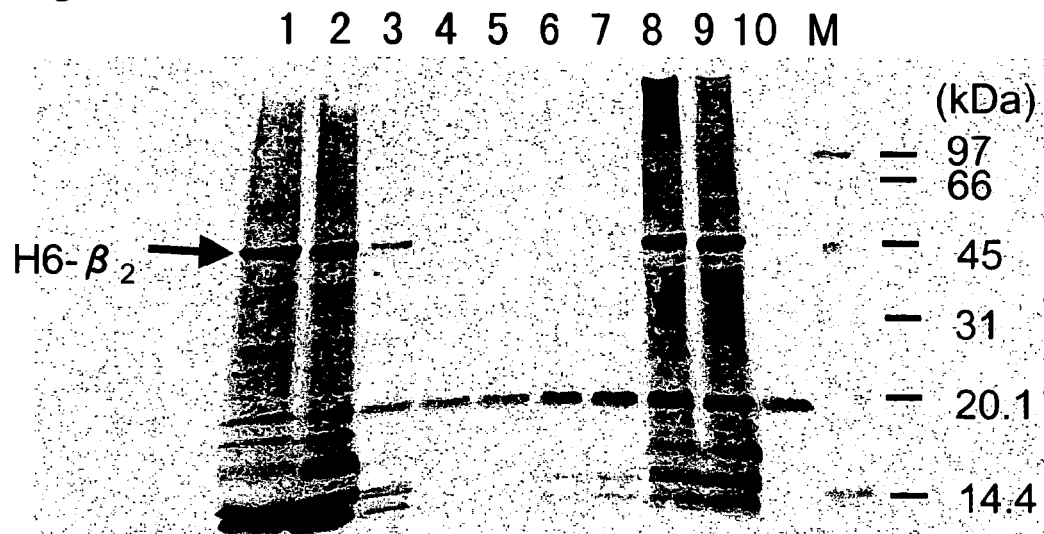
FIG. 7 shows the results of SDS-Polyacrylamide Gel Electrophoresis of human β2-adrenergic receptor (ADRB2) synthesized in cell-free protein synthesis system comprising Brij35, by the western blotting analysis. Insoluble fractions precipitated by centrifugation after synthesis reactions were applied on lanes 1 to 5, and the supernatant fractions of the centrifugation were applied on lanes 6 to 10. The amounts of Brij35 added to the reaction mixture were 0% (lanes 1 and 6), 0.01% (lanes 2 and 7), 0.02% (lanes 3 and 8), 0.2% (lanes 4 and 9) and 0% without template DNAs (lanes 5 and 10), respectively. Lane M was the molecular weight marker (ECL protein molecular weight markers by Amersham Pharmacia Biotech).

The result of Western blotting analysis of proteins synthesized in the presence or absence of Brij35 was shown in FIG. 7. In the absence of Brij35 and in the presence of 0.01% Brij35, the synthesized His6-$\beta_2$ was insoluble (lanes 1 and 2), and was not detected in the supernatant (lanes 6 and 7). In the presence of 0.02% Brij35, although a portion of the synthesized His6-$\beta_2$ was detected in the insoluble fraction (lane 3), most of the proteins were detected in the supernatant fraction (lane 8). In the presence of 0.2% Brij35, only a small amount of His6-$\beta_2$ was insoluble (lane 4), and almost all amount of the protein were detected in the supernatant (lane 9). These results indicated that a membrane protein His6-$\beta_2$ could be recovered from the supernatant in the system using Brij35 as well as that of digitonin. Incidentally, about 20 kDa bands were detected in all samples including control samples (lanes 5 and 10) without template DNA, thus, they are considered to be proteins derived from E. coli, to which the antibody binds nonspecifically.

Synthesis of His6-$\beta_2$ Protein by Addition of $\beta$-dodecylmaltoside, NP-40, Tween 20 or Triton X-100

Figure 8:
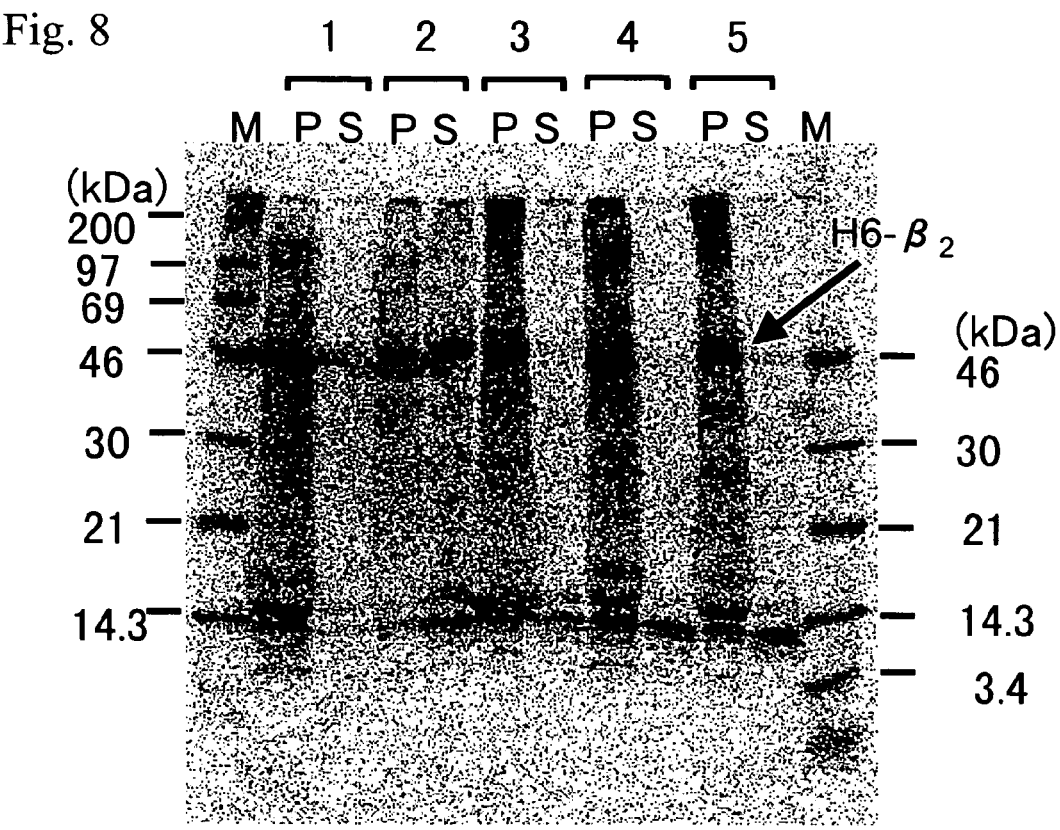
FIG. 8 shows the results of SDS-Polyacrylamide Gel Electrophoresis of human β2-adrenergic receptor (ADRB2) synthesized in cell-free protein synthesis system comprising β-dodecylmaltoside, NP-40, Tween 20 or Triton X-100, and analyzed by autoradiography. Samples synthesized by adding no detergent, 0.5% each of β-dodecylmaltoside, NP-40, Tween 20, Triton X-l00 were applied on lanes 1 to 5, respectively. P shows insoluble fractions, and S shows supernatant fractions. Lane M was the molecular weight marker (ECL protein molecular weight markers by Amersham Pharmacia Biotech).
Figure 9:
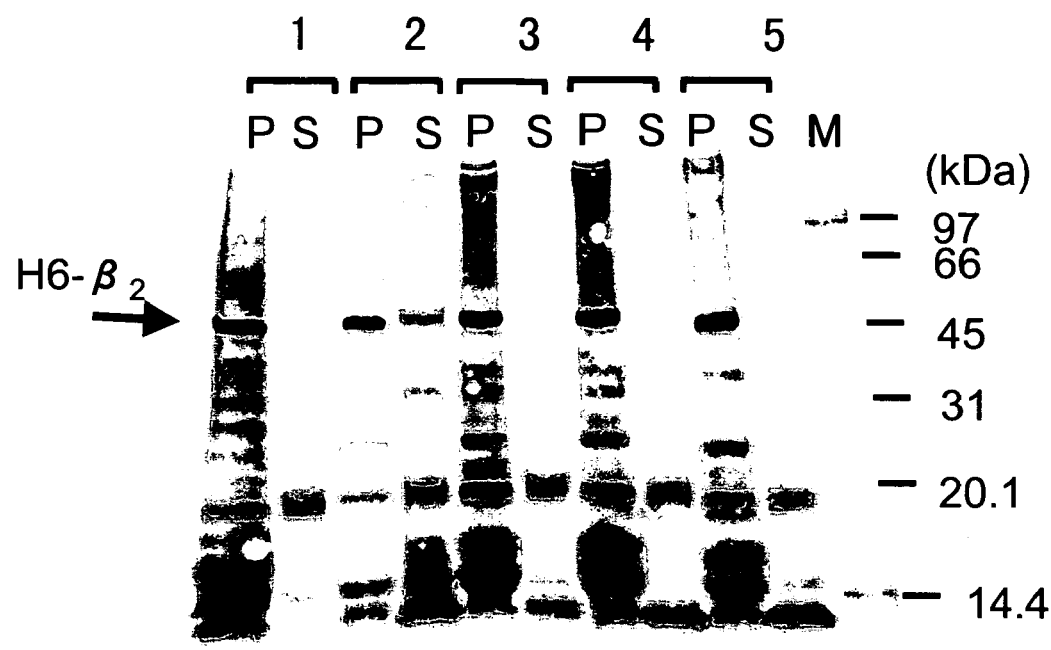
FIG. 9 shows the results of SDS-Polyacrylamide Gel Electrophoresis of human β2-adrenergic receptor (ADRB2) synthesized in cell-free protein synthesis system comprising β-dodecylmaltoside, NP-40, Tween 20 or Triton X-100, and analyzed by the western blotting analysis. Samples synthesized by adding no detergent, 0.5% each of β-dodecylmaltoside, NP-40, Tween 20, Triton X-100 were applied on lanes 1 to 5, respectively. P shows insoluble fractions, and S shows supernatant fractions. Lane M was the molecular weight marker (ECL protein molecular weight markers by Amersham Pharmacia Biotech).

The result of autoradiography of proteins synthesized in case of adding $\beta$-dodecylmaltoside, NP-40, Tween20 or Triton X-100 to the reaction mixture so that the final concentration thereof was 0.5% was shown in FIG. 8, and also the result of Western blotting analysis of that was shown in FIG. 9. In both FIG. 8 and FIG. 9, the bands corresponding to molecular weight about 46000 are speculated to be His6-$\beta_2$ protein. These results indicated that, in the absence of detergent (surfactant), the protein was detected in the precipitate fraction only (lane 1P), and was not detected in the supernatant fraction (lane 1S). In contrast, in the presence of various detergents, almost same amounts of His6-$\beta_2$ proteins were detected in the insoluble fraction (lane 2P) and the supernatant fraction (lane 2S) in case of adding 0.5% $\beta$-dodecylmaltoside. Incidentally, in case of adding the other detergents, His6-$\beta_2$ protein was little detected in the supernatant fraction. These results indicated that a membrane protein His6-$\beta_2$ could be recovered from the supernatant by adding 0.5% $\beta$-dodecylmaltoside.

Example 3

Reconstitution of a Human $\beta$-adrenergic Receptor (ADRB2)

Protein Synthesis by Dialysis Method

A template cDNA fragment for expression of human $\beta$2-adrenergic receptor (ADRB2) was prepared according to the same manner as Example 2, and further cloned into plasmid pCR2.1-TOPO by using TOPO TA Cloning Kit (Invitrogen Co.) to use as a template. Next, His6-$\beta_2$ protein was synthesized by cell free protein synthesis system using E. coli S30 extract according to the same method as Example 1. However, in contrast to Example 1 and 2, the protein synthesis was performed by the dialysis method using an internal reaction mixture (20 mL) and an external reaction mixture (200 mL), whose compositions were shown in Table 5. The internal mixture was dispensed with 5 mL each in four dialysis membranes (DispoDialyzer, Spectra/Por, fraction molecular weight 50000), and was suspended in the external reaction mixture for synthesizing protein at 30° C. for 16 hours.

TABLE 5

| | Concentration | |
|---|---|---|
| Composition | Internal dialysate | External dialysate |
| Hepes-KOH (pH7.5) | 58.0 mM | 58.0 mM |
| Dithiothreitol | 2.3 mM | 2.3 mM |
| ATP | 1.2 mM | 1.2 mM |
| CTP, GTP, UTP | Each 0.9 mM | Each 0.9 mM |
| Creatine phosphate | 81.0 mM | 81.0 mM |
| Creatine kinase | 250.0 µg/mL | 250.0 µg/mL |
| Polyethylene glycol 8000(PEG8000) | 4.00% (w/v) | 4.00% (w/v) |

TABLE 5-continued

| Composition | Concentration | |
| --- | --- | --- |
| | Internal dialysate | External dialysate |
| cyclic AMP(cAMP) | 0.64 mM | 0.64 mM |
| L-(−)-5-5,6,7,8-tetrahydrofolate | 35.0 µg/mL | 35.0 µg/mL |
| E. coli total t-RNA | 170.0 µg/mL | 170.0 µg/mL |
| Potassium glutamate | 200.0 mM | 200.0 mM |
| Ammonium acetate | 27.7 mM | 27.7 mM |
| Magnesium acetate | 10.7 mM | 10.7 mM |
| Sodium azide | 1.5 mM | 1.5 mM |
| 20 kinds of amino acid | Each 1.5 mM | Each 1.5 mM |
| T7 RNA polymerase (Toyobo) | 16.0 units/µL | — |
| E. coli S30 extract | 7.2 µL/30 µL of total volume | — |
| Plasmid DNA | 1.0 µL/30 µL of total volume | — |
| Digitonin | 0.4% | 0.4% |
| Lipid solution | 0.5 µL/30 µL of total volume | — |
| Potassium acetate | — | 3.0 mM |
| Tris-acetate | — | 4.2 mM |

Dialysis

After the synthesis reaction, the above dialysis membranes were transferred into phosphate buffer (137 mM NaCl, 2.7 mM KCl, 10 mM $Na_2HPO_4$, 2 mM $KH_2PO_4$), containing 1% CARBIOSORB (Carbiochem), for performing dialysis at 4° C. for 8 hours while replacing the buffer every two to three hours.

Solubilization

After the dialysis, the internal dialysate was recovered, and ultracentrifuged at 100,000×g for one hour at 4° C. The precipitate fraction thus obtained was suspended in 15 mL of the above phosphate buffer, and supplemented by drop with 10% β-dodecylmaltoside (NacalaiTesque Inc.) to adjust 1% of the final concentration, and then was solubilized at 4° C. for 2 hours. The solubilized solution was transferred into dialysis membrane tube (Spectra/Por, fraction molecular weight 10,000), and was dialyzed in the above phosphate buffer at 4° C. for 8 hours.

Purification

The solubilized solution after dialysis was ultracentrifuged at 4° C., 100000×g for one hour. The supernatant fraction thus obtained (15 mL) was added with Ni—NTA agarose (QIAGEN) (wet volume 2 mL) which was pre-equilibrated with buffer A (20 mM phosphate buffer (pH7.4), 500 mM NaCl, 10 mM imidazole, 0.05% β-dodecylmaltoside), and then mixed gently at 4° C. for 3 hours. Next, the Ni—NTA agarose was packed to a column for removing the extra buffer therefrom. After washing the column with 20 mL of buffer A, the protein was eluted with 5 mL of buffer B (20 mM phosphate buffer (pH7.4), 500 mM NaCl, 300 mM imidazole, 0.05% β-dodecylmaltoside).

Desalting 5 mL of the protein eluate was concentrated by VIVASPIN (Sartorius K. K., fraction molecular weight 10000) up to 2.5 ml. 2.5 mL of the concentrate was added to PD-10 desalting column (Amersham Pharmacia) pre-equilibrated with phosphate buffer, followed by adding phosphate buffer to the column to recover an eluate fraction of protein (3.5 mL).

Reconstitution 3.5 mL of the protein eluate was concentrated by VIVASPIN (fraction molecular weight 10000) up to 1 ml. To this 1 mL concentrate, 0.01% β-dodecylmaltoside in final concentration and 6.25 µL of mixed lipid solution was added, and the mixture was transferred to dialysis membrane tube (Spectra/Por, fraction molecular weight 50000) for dialyzing in phosphate buffer containing 1% CARBIOSORB at 4° C. for 8 hours.

Detection of the Reconstituted His6-$β_2$Protein

Figure 10:
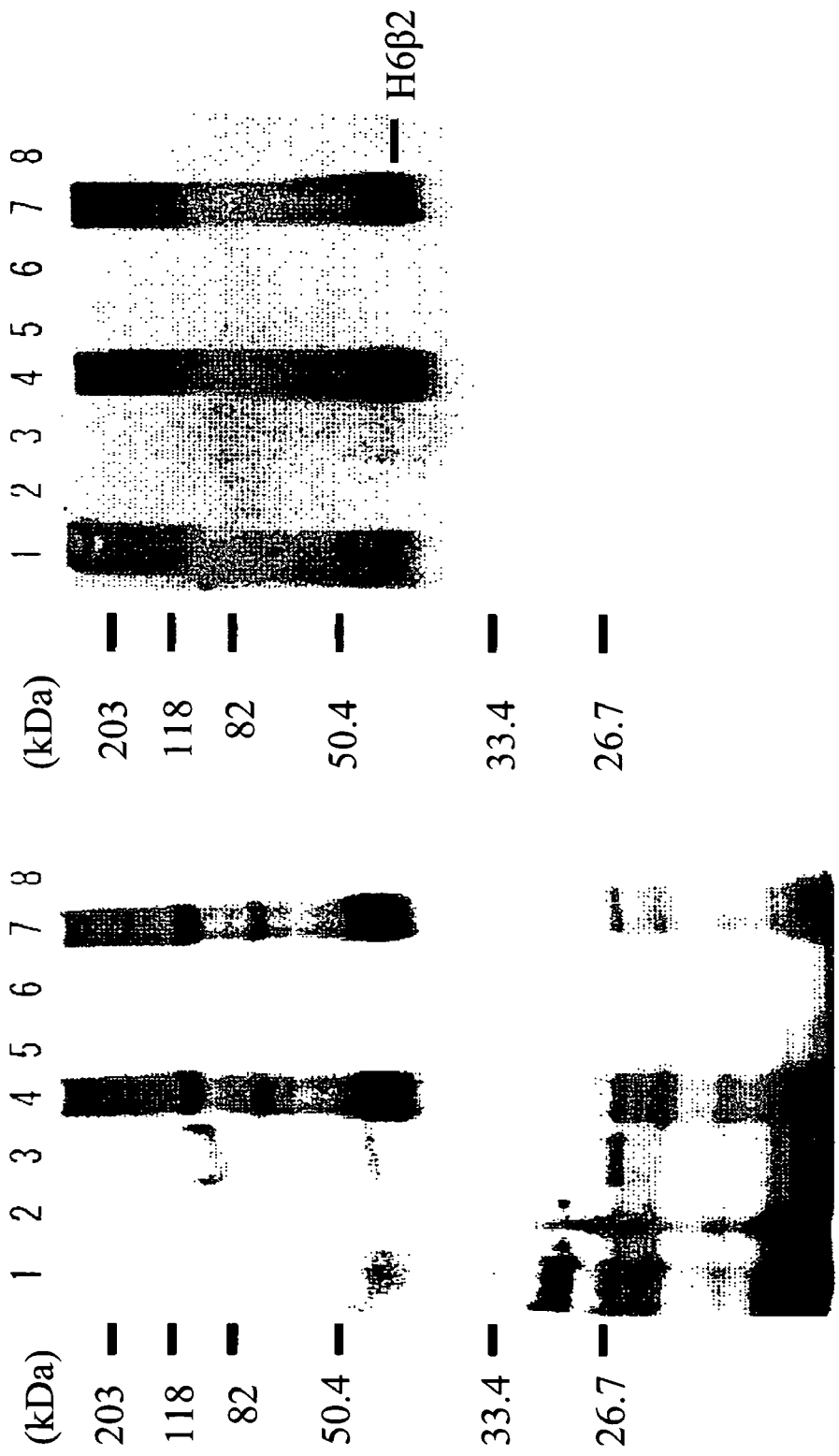
FIG. 10 shows the results of SDS-Polyacrylamide Gel Electrophoresis of respective purification steps of human β2-adrenergic receptor (ADRB2) reconstituted by the method shown in Example 3, and analyzed by (a) silver staining, and (b) the western blotting analysis. Samples of purification steps by Ni—NTA agarose column, and those by PD-10 desalting column were applied on lanes 1 to 5 (1:crude sample, 2:flow through fraction, 3:wash out fraction, 4:eluted fraction with 300 mM imidazole, 5:eluted fraction with 500 mM imidazole), and lanes 6 to 8 (6:flow through fraction, 7:fraction No.1, 8:fraction No.2), respectively.

The purity of His6-$β_2$ protein reconstituted in the presence of detergent and lipid according to the above method was analyzed by SDS-PAGE and Western blotting by the same method of Examples 1 and 2. FIG. 10 shows the results of subjecting samples in each step of purification by Ni-NTA agarose and PD-10desalting column to (a) silver staining, and (b) the western blotting analysis using anti β2 AR antibody, after SDS-PAGE Both results of (a) and (b) indicates that His6-$β_2$ protein (molecular weight about 46 kDa) was purified.

Binding Assay

The dialyzed protein solution reconstituted by the above methods was ultracentrifuged at 4° C., 100,000×g for one hour. The obtained precipitate fraction (the reconstituted membrane fraction) was suspended in 100 to 200 µL of incubation buffer (75 mM Tris-HCI (pH7.4), 12.5 mM $MgCl_2$, 2 mM EDTA). This reconstituted membrane fraction was allowed to stand in the presence of 0 to 100 µM of Alprenolol (Sigma Co.) at 30° C. for 30 minutes. Subsequently, [$^3$H]Dihidroalprenolol was added thereto as to make up 10 µM of the final concentration, and further reacted at 30° C. for one hour.

Figure 11:
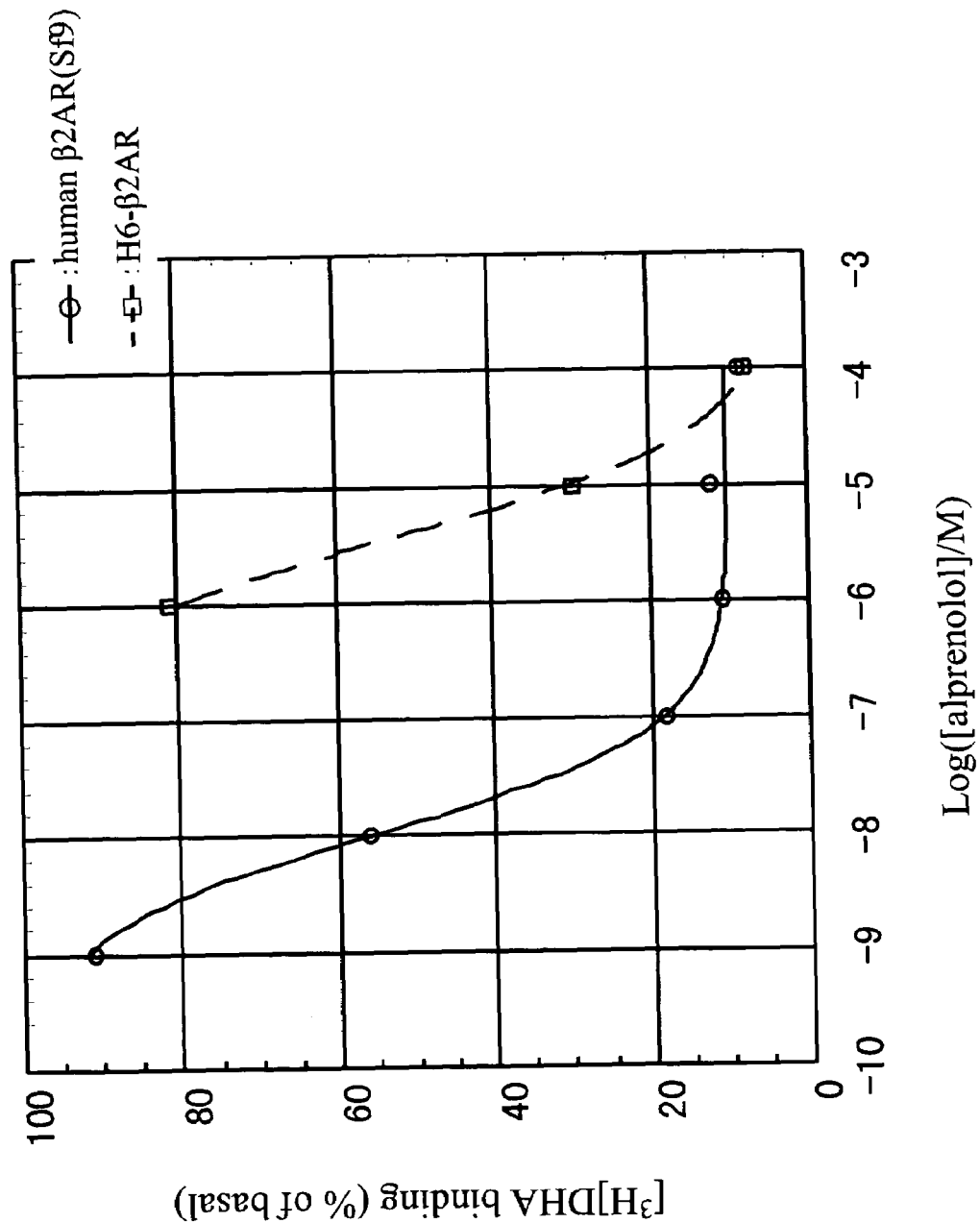
FIG. 11 shows binding curves of the His6-$β_2$ protein reconstituted in Example 3 and human β2-adrenergic receptor (Sf9) used as a control to Alprenolol.

96 well Unifilter GF/C (Whatman) was prepared, and previously washed two times with 200 µL of 0.3% polyethyleneimine, and subsequently nine times with 200 µL of 50 mM Tris-HCl (pH7.4). To this 96 well Unifilter, the above reaction mixture was added, and subsequently washed seven times with incubation buffer. Then, the 96 well Unifilter was dried, and to each well of the dried Unifilter, 50 µL of MicroScint-0 (Packard) was added. This Unifilter was allowed to stand in a dark place for 10 minutes. The radioactivities derived from [$^3$H]Dihidroalprenolol of respective wells of this Unifilter were determined by using TOPCOUNT (Packard). The incorporated amount of [$^3$H] Dihidroalprenolol in the presence of various concentration of Alprenolol (Binding Curve) was shown in FIG. 11. In FIG. 11, the human β2AR (Sf9) (Lot No. UHW-1098F) used as a control was purchased from RBI. In FIG. 11, a molar concentration of added Alprenolol was plotted on the x-axis in a log scale, and an incorporated ratio of radioactivity in the presence of respective concentrations of Alprenolol in case of taking a radioactivity determined in the absence of Alprenolol as 100% was plotted on y-axis. From FIG. 11, it is found that, the efficiency of incorporation of [$^3$H]Dihidroalprenolol into His6-$β_2$ protein reconstituted by the method of the present invention, decreases from about 80% to about 10% according as the concentration of Alprenolol increases from $10^{-6}$M to $10^{-4}$M, that is, the protein binds to the added non-labeled Alprenolol.

INDUSTRIAL APPLICABILITY

According to the present invention, it is capable of obtaining a constant amount of protein, especially membrane protein, without loss of activity of the protein, and providing a useful method for the research of structure and function of the protein. Through the development of drugs to control the function of these membrane protein, in particular, a receptor, channel protein and transporter, a variety of applications for diagnostics and treatment are expected.

The invention claimed is:

1. A method for producing an eukaryotic membrane protein using a cell-free protein synthesis system comprising a detergent to synthesize the protein without aggregation, wherein the detergent is digitonin in an amount of 0.4 to 1.5% by volume or polyoxyethylene 23 lauryl ether in an amount of 0.02 to 0.2% by volume, or a mixture of digitonin in an amount of 0.4 to 1.5% by volume and polyoxyethylene 23 lauryl ether in an amount of 0.02 to 0.2% by volume.

2. The method of claim 1, wherein said membrane protein is a protein that comprises a hydrophobic region, or said membrane protein is a portion of said membrane protein comprising a hydrophobic region.

3. A method for reconstituting a protein produced in a cell-free protein synthesis system comprising a nucleic acid template coding for at least a portion of a membrane protein comprising a hydrophobic region, a detergent that is digitonin in an amount of 0.4 to 1.5% by volume or polyoxyethylene 23 lauryl ether in an amount of 0.02 to 0.2% by volume, or a mixture of digitonin in an amount of 0.4 to 1.5% by volume and polyoxyethylene 23 lauryl ether in an amount of 0.02 to 0.2% by volume, and a lipid, wherein said protein is reconstituted in a lipid bilayer by decreasing the concentration of said detergent in said system simultaneously with the protein synthesis or after a period therefrom.

4. The method of claim 3, wherein the step of decreasing the concentration of said detergent is performed by any one or more methods selected from the group consisting of dialysis, dilution, filtration, centrifugation and addition of an adsorbent to said detergent.

5. A method for producing a membrane protein comprising the steps of:

(a) synthesizing the protein in a cell-free protein synthesis system comprising a cell extract, a nucleic acid template coding for said protein, a detergent that is digitonin in an amount of 0.4 to 1.5% by volume or polyoxyethylene 23 lauryl ether in an amount of 0.02 to 0.2% by volume, or a mixture of digitonin in an amount of 0.4 to 1.5% by volume or polyoxyethylene 23 lauryl ether in an amount of 0.02 to 0.2% by volume and a lipid; and (b) decreasing the concentration of said detergent in the reaction mixture simultaneously with the protein synthesis or after a period therefrom, wherein the synthesized protein has at least a part of its biological activity.

6. The method of claim 5, wherein said membrane protein is a protein selected from the group consisting of a receptor, a channel protein, a transporter, and a membrane-bound enzyme.

7. The method of claim 3, wherein said cell-free protein synthesis system comprises a bacterial cell extract.

8. The method of claim 5, wherein said cell extract is a bacterial cell extract.

9. The method of claim 1, wherein said eukaryotic membrane protein is a G protein coupled receptor.

10. The method of claim 3, in which the protein is a G protein coupled receptor.

11. The method of claim 5, in which the protein is a G protein coupled receptor.

* * * * *

SEQUENCE LISTING

<160> NUMBER OF SEQ ID NOS: 9

<210> SEQ ID NO 1
<211> LENGTH: 52
<212> TYPE: DNA
<213> ORGANISM: Artificial Sequence
<220> FEATURE:
<223> OTHER INFORMATION: Description of Artificial Sequence:NTR-5'
      primer

<400> SEQUENCE: 1
gtttaacttt aagaaggaga tatacatatg aaaataaaaa caggtgcacg ca          52

<210> SEQ ID NO 2
<211> LENGTH: 50
<212> TYPE: DNA
<213> ORGANISM: Artificial Sequence
<220> FEATURE:
<223> OTHER INFORMATION: Description of Artificial Sequence:NTR-3'
      primer

<400> SEQUENCE: 2
gcggataaca atttcacaca ggaaacagtc gacgccaggg ttttcccagt             50

<210> SEQ ID NO 3
<211> LENGTH: 136
<212> TYPE: DNA
<213> ORGANISM: Artificial Sequence
<220> FEATURE:
<223> OTHER INFORMATION: Description of Artificial Sequence:NTR-5'
      fragment

<400> SEQUENCE: 3
ccgctgtcct cgttcccagc ccatgattac gaattcagat ctcgatcccg cgaaattaat   60
acgactcact atagggagac cacaacggtt tccctctaga ataatttttg tttaacttta  120
agaaggagat atacat                                                  136

<210> SEQ ID NO 4
<211> LENGTH: 183
<212> TYPE: DNA
<213> ORGANISM: Artificial Sequence
<220> FEATURE:
<223> OTHER INFORMATION: Description of Artificial Sequence:NTR-3'
      fragment

<400> SEQUENCE: 4
gtttcctgtg tgaaattgtt atccgctgct gagttggctg ctgccaccgc tgagcaataa   60
ctagcataac cccttggggc ctctaaacgg gtcttgaggg gttttttgct gaaaggagga  120
actatatccg gataacctcg agctgcaggc atgcaagctt ggggctggga acgaggacag  180
cgg                                                                183

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence:NTR-5'3'
      primer

<400> SEQUENCE: 5
gccgctgtcc tcgttcccag cc                                           22

```
<210> SEQ ID NO 6
<211> LENGTH: 34
<212> TYPE: DNA
<213> ORGANISM: Artificial Sequence
<220> FEATURE:
<223> OTHER INFORMATION: Description of Artificial Sequence:ADR2-5'
      primer

<400> SEQUENCE: 6
ggtgccacgc ggatccatgg ggcaacccgg gaac                              34

<210> SEQ ID NO 7
<211> LENGTH: 61
<212> TYPE: DNA
<213> ORGANISM: Artificial Sequence
<220> FEATURE:
<223> OTHER INFORMATION: Description of Artificial Sequence:ADR2-3'
      primer

<400> SEQUENCE: 7
gcggataaca atttcacaca ggaaacagtc gacttacagc agtgagtcat ttgtactaca   60
a                                                                  61

<210> SEQ ID NO 8
<211> LENGTH: 193
<212> TYPE: DNA
<213> ORGANISM: Artificial Sequence
<220> FEATURE:
<223> OTHER INFORMATION: Description of Artificial Sequence:ADR2 5'
      fragment

<400> SEQUENCE: 8
ccgctgtcct cgttcccagc ccatgattac gaattcagat ctcgatcccg cgaaattaat   60
acgactcact atagggagac cacaacggtt tccctctaga aataattttg tttaacttta  120
agaaggagat atacatatgg gcagcagcca tcatcatcat catcacagca gcggcctggt  180
gccacgcgga tcc                                                    193

<210> SEQ ID NO 9
<211> LENGTH: 183
<212> TYPE: DNA
<213> ORGANISM: Artificial Sequence
<220> FEATURE:
<223> OTHER INFORMATION: Description of Artificial Sequence:ADR2 3'
      fragment

<400> SEQUENCE: 9
gtttcctgtg tgaaattgtt atccgctgct gagttggctg ctgccaccgc tgagcaataa   60
ctagcataac cccttggggc ctctaaacgg gtcttgaggg gttttttgct gaaaggagga  120
actatatccg gataacctcg agctgcaggc atgcaagctt ggggctggga acgaggacag  180
cgg                                                               183
```